(12) United States Patent
Keidar

(10) Patent No.: US 8,021,387 B2
(45) Date of Patent: Sep. 20, 2011

(54) TRANS-SEPTAL SHEATH WITH SPLITTING DILATING NEEDLE AND METHOD FOR ITS USE

(75) Inventor: Yaron Keidar, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 805 days.

(21) Appl. No.: 10/618,033

(22) Filed: Jul. 11, 2003

(65) Prior Publication Data

US 2005/0113860 A1     May 26, 2005

(51) Int. Cl.
*A61M 29/00*     (2006.01)

(52) U.S. Cl. ........................................ 606/198; 606/167

(58) Field of Classification Search ........... 606/198, 606/167, 187, 119, 181, 191, 184–185, 99, 606/108; 604/106; 600/114, 184–185, 190, 600/194, 201, 204, 206, 208, 210, 211, 214, 600/219, 235
See application file for complete search history.

(56) References Cited

U.S. PATENT DOCUMENTS

| | | | | |
|---|---|---|---|---|
| 668,879 A * | 2/1901 | Miller | ............................ | 27/21.1 |
| 765,879 A * | 7/1904 | Campbell | ..................... | 606/198 |
| 2,072,346 A * | 3/1937 | Smith | ............................. | 27/24.2 |
| 2,485,939 A * | 10/1949 | Tedford | ........................ | 606/198 |
| 3,397,699 A * | 8/1968 | Kohl | ............................. | 604/105 |
| 3,713,447 A * | 1/1973 | Adair | ............................ | 604/105 |
| 3,799,172 A * | 3/1974 | Szpur | ........................... | 604/105 |
| 3,946,741 A * | 3/1976 | Adair | ............................ | 604/105 |
| 3,991,756 A * | 11/1976 | Synder | .......................... | 604/513 |
| 4,350,151 A | 9/1982 | Scott | | |
| 4,520,810 A * | 6/1985 | Weiss | ....................... | 128/207.29 |
| 4,553,542 A * | 11/1985 | Schenck et al. | ............... | 606/153 |
| 4,608,965 A * | 9/1986 | Anspach et al. | .............. | 600/101 |
| 4,863,430 A * | 9/1989 | Klyce et al. | ............. | 604/170.03 |
| 4,877,021 A * | 10/1989 | Higer et al. | .............. | 128/200.26 |
| 4,976,684 A * | 12/1990 | Broadnax, Jr. | ................ | 604/540 |
| 5,041,093 A * | 8/1991 | Chu | .............................. | 604/104 |
| 5,053,009 A * | 10/1991 | Herzberg | ....................... | 604/104 |
| 5,123,905 A * | 6/1992 | Kelman | ........................ | 606/107 |

(Continued)

FOREIGN PATENT DOCUMENTS

WO     WO 9936015 A1 *    7/1999

(Continued)

OTHER PUBLICATIONS

European Search Report dated Nov. 8, 2004 from European Patent Application No. 04254120.1.

*Primary Examiner* — Gary Jackson
*Assistant Examiner* — Erin Colello
(74) *Attorney, Agent, or Firm* — Christie, Parker & Hale, LLP

(57) ABSTRACT

A device useful for accessing the left atrium is provided. The device comprises an elongated tubular body and a dilating tip. The tubular body has an axis, a proximal end, a distal end and a lumen longitudinally extending therethrough. The dilating tip is slidably mounted on the distal end of the tubular body. The dilating tip comprises a segmented surface that is generally transverse to the axis of the tubular body, and a generally rigid tube extending distally from the segmented surface and having a sharp distal end. Distal movement of the tubular body relative to the dilating tip exerts a force on the segmented surface to thereby open the segmented surface.

17 Claims, 4 Drawing Sheets

U.S. PATENT DOCUMENTS

| | | | | |
|---|---|---|---|---|
| 5,312,341 A | | 5/1994 | Turi | |
| 5,320,627 A | * | 6/1994 | Sorensen et al. | 606/128 |
| 5,454,365 A | * | 10/1995 | Bonutti | 600/204 |
| 5,505,690 A | * | 4/1996 | Patton et al. | 600/210 |
| 5,509,893 A | * | 4/1996 | Pracas | 600/224 |
| 5,562,677 A | * | 10/1996 | Hildwein et al. | 606/108 |
| 5,575,766 A | | 11/1996 | Swartz et al. | |
| 5,683,451 A | * | 11/1997 | Lenker et al. | 623/1.11 |
| 5,685,826 A | * | 11/1997 | Bonutti | 600/204 |
| 5,800,450 A | | 9/1998 | Lary et al. | |
| 5,814,073 A | * | 9/1998 | Bonutti | 606/232 |
| 5,817,062 A | * | 10/1998 | Flom et al. | 604/174 |
| 5,888,196 A | * | 3/1999 | Bonutti | 600/204 |
| 5,965,089 A | | 10/1999 | Jarvik et al. | |
| 5,971,960 A | * | 10/1999 | Flom et al. | 604/174 |
| 6,027,518 A | * | 2/2000 | Gaber | 606/198 |
| 6,030,364 A | | 2/2000 | Durgin et al. | 604/164.01 |
| 6,099,511 A | | 8/2000 | Devos et al. | 604/246 |
| 6,217,549 B1 | * | 4/2001 | Selmon et al. | 604/106 |
| 6,254,628 B1 | * | 7/2001 | Wallace et al. | 623/1.12 |
| 6,280,379 B1 | * | 8/2001 | Resnick | 600/220 |
| 6,287,322 B1 | * | 9/2001 | Zhu et al. | 606/213 |
| 6,436,119 B1 | * | 8/2002 | Erb et al. | 606/198 |
| 6,451,042 B1 | * | 9/2002 | Bonutti | 606/190 |
| 6,530,896 B1 | * | 3/2003 | Elliott | 604/60 |
| 6,638,247 B1 | * | 10/2003 | Selmon et al. | 604/104 |
| 6,676,665 B2 | * | 1/2004 | Foley et al. | 606/105 |
| 6,849,064 B2 | * | 2/2005 | Hamada | 604/164.01 |
| 6,855,126 B2 | * | 2/2005 | Flinchbaugh | 604/106 |
| 6,939,318 B2 | * | 9/2005 | Stenzel | 604/60 |
| 2002/0128636 A1 | | 9/2002 | Chin et al. | |
| 2002/0161424 A1 | | 10/2002 | Rapacki et al. | |
| 2002/0169377 A1 | * | 11/2002 | Khairkhahan et al. | 600/433 |
| 2002/0193822 A1 | * | 12/2002 | Hung et al. | 606/198 |
| 2003/0009185 A1 | * | 1/2003 | Jessen | 606/167 |
| 2003/0050637 A1 | | 3/2003 | Maguire et al. | |
| 2003/0083613 A1 | | 5/2003 | Schaer | |
| 2005/0222599 A1 | * | 10/2005 | Czernecki et al. | 606/182 |
| 2006/0079925 A1 | * | 4/2006 | Kerr | 606/198 |
| 2006/0106415 A1 | * | 5/2006 | Gabbay | 606/198 |
| 2006/0167487 A1 | * | 7/2006 | Hamada | 606/198 |
| 2006/0287574 A1 | * | 12/2006 | Chin | 600/114 |
| 2008/0142566 A1 | * | 6/2008 | Gresham et al. | 227/179.1 |

FOREIGN PATENT DOCUMENTS

| | | | |
|---|---|---|---|
| WO | WO 02/058780 A1 | | 8/2002 |
| WO | WO 02/094363 A2 | | 11/2002 |
| WO | WO 2006127784 A2 | * | 11/2006 |

* cited by examiner

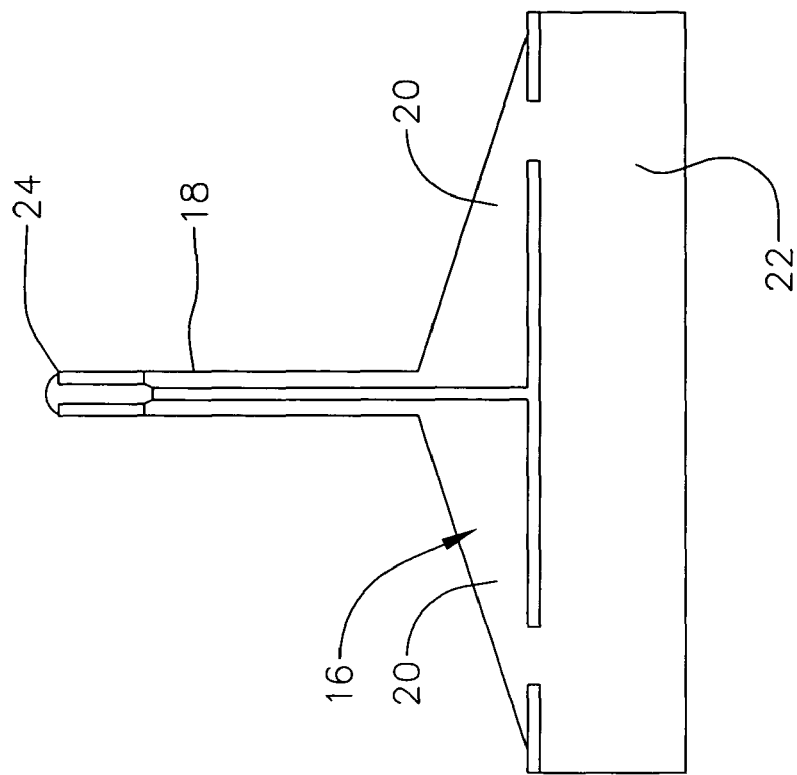
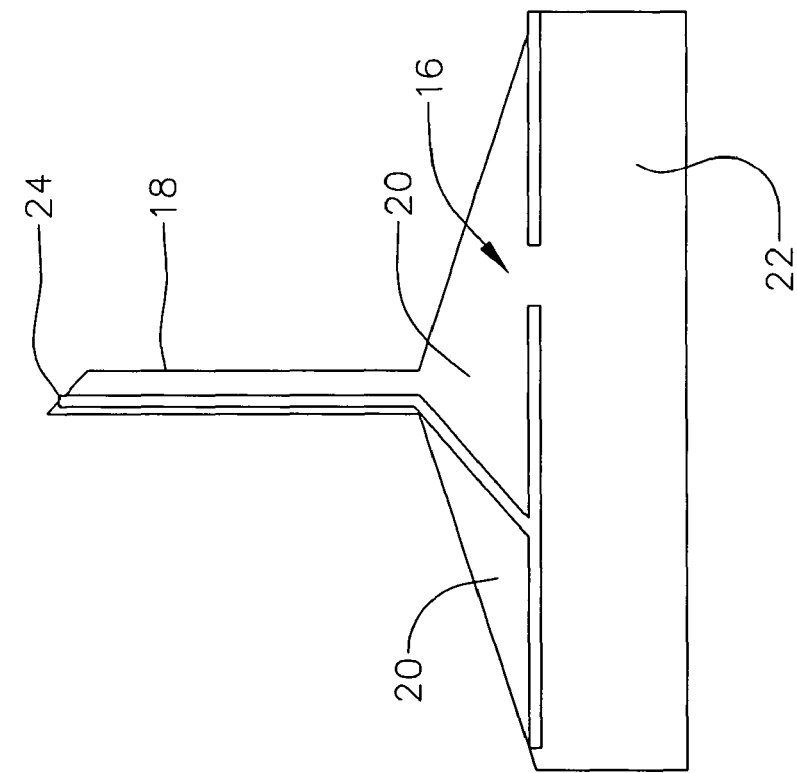

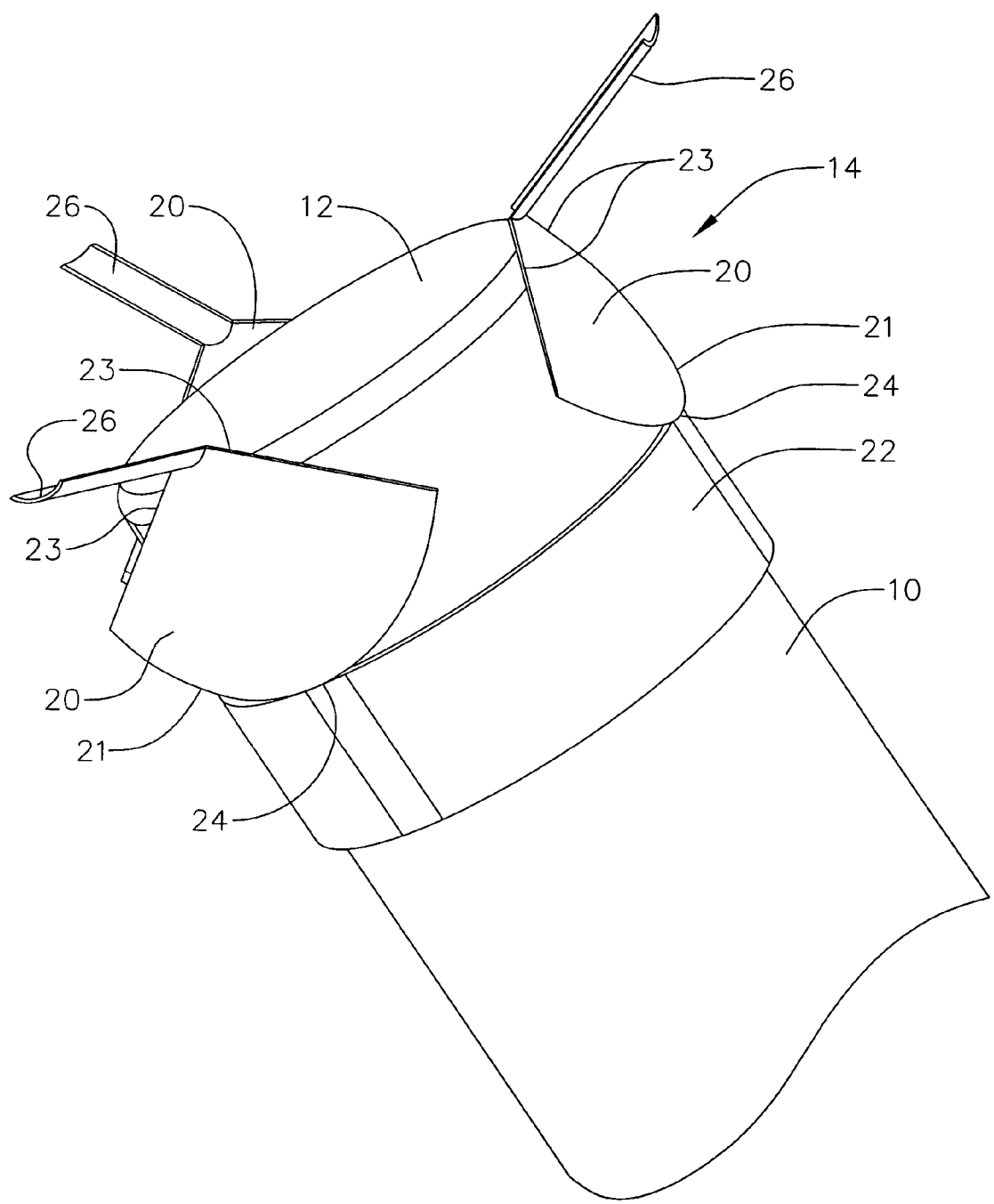

TRANS-SEPTAL SHEATH WITH SPLITTING DILATING NEEDLE AND METHOD FOR ITS USE

FIELD OF THE INVENTION

The present invention is directed to a device that functions as both a guiding sheath and dilating needle.

BACKGROUND OF THE INVENTION

Electrophysiology catheters are commonly used for mapping electrical activity in a heart. Electrophysiology is a specialty within the field of cardiology for diagnosis and treatment of electrical abnormalities of the heart. By mapping the electrical activity in the heart, ectopic sites of electrical activation or other electrical activation pathways that contribute to heart malfunctions may be detected. This type of information may then allow a cardiologist to intervene and destroy the malfunctioning heart tissues. Such destruction of heart tissue is typically performed using an ablation catheter and is referred to as ablation. Ablation is a rapidly growing field within electrophysiology and obviates the need for maximally invasive open heart surgery.

Occasionally, an electrical abnormality occurs in a location that is difficult to reach with standard catheter capabilities. A left atrium of a heart is one such location. When an electrical abnormality occurs in a left atrium, a dilation catheter, or dilator, may be inserted percutaneously, fed through one or more major blood vessels, and inserted into a right atrium of the heart. A needle may then be feed through the dilator and inserted into and through the atrial septum to puncture the atrial septum to allow access to the left atrium for a therapeutic catheter, such as an ablation catheter.

A current technique for puncturing the atrial septum includes positioning a dilator adjacent to an area of the atrial septum that is desired to be punctured (typically at the fosa ovalis), inserting a separate needle into the dilator, feeding the needle through the dilator until the needle protrudes beyond the dilator, and puncturing the atrial septum with the needle. This technique has several disadvantages. For example, locating the desired puncture site and then inserting and feeding a separate needle into the dilator increases the procedure time, and increases the likelihood that the dilator will be inadvertently moved before the needle reaches the desired puncture site, thus requiring a repositioning of the dilator. If the repositioning is performed with the needle inside the dilator, the possibility exists for the needle to slide out of the dilator and damage venous or atrial structures. If the needle is removed during repositioning, procedure time is again extended during reinsertion and re-feeding of the needle into the dilator, and an inadvertent movement of the dilator during reinsertion and re-feeding of the needle again exists.

Another more serious disadvantage of the current technique is that, to dilate the hole enough for a guiding sheath to fit through with the dilator, the sharp needle has to be advanced ten to twenty millimeters into the left atrium, which would bring the sharp edge dangerously close to the superior wall of the left atrium, which might result in perforation, especially if the left atrium is small. Moreover, a force in a distal direction is required to insert the needle into and through the atrial septum, yet there is no means for controlling the maximum protrusion of the needle from the dilator. As a result, a tendency is for the operator to continue to apply a forward force to the needle even after the needle has crossed the atrial septum, thus risking damage to venous or atrial structures in the left atria or even cardiac puncture if the needle protrudes too far from the dilator.

Yet another disadvantage of the existing technique is that, when the sheath is advanced into the left atrium, it is typically placed at least about ten millimeters beyond the septum wall. If it is advanced less than ten millimeters, it might fall out of the left atrium. This gives catheters and other devices that go through the sheath very limited access to the septum from the left side. If a procedure requires mapping or ablation on the left septum, it is almost impossible to perform with conventional sheaths.

SUMMARY OF THE INVENTION

The present invention addresses the above-referenced problems by providing a device useful for accessing the left atrium. The device comprises an elongated tubular body and a dilating tip. The tubular body has an axis, a proximal end, a distal end and a lumen longitudinally extending therethrough. The dilating tip is slidably mounted on the distal end of the tubular body. The dilating tip comprises a segmented surface that is generally transverse to the axis of the tubular body, and a generally rigid tube extending distally from the segmented surface and having a sharp distal end. Distal movement of the tubular body relative to the dilating tip exerts a force on the segmented surface to thereby open the segmented surface.

In another embodiment, the invention is directed to a device useful for accessing the left atrium comprising an elongated tubular body and a dilating tip. The tubular body has an axis, a proximal end, a distal end and a lumen longitudinally extending therethrough. The dilating tip is slidably mounted on the distal end of the tubular body. The dilating tip comprises a ring mounted in surrounding relating to the distal end of the tubular body and a segmented surface that is generally transverse to the axis of the tubular body. The segmented surface comprises three or more segments, each segment being hingedly attached to the ring. The dilating tip further comprises a generally rigid tube extending distally from the segmented surface. The tube has a sharp distal end and is segmented into three or more segments. Distal movement of the tubular body relative to the dilating tip exerts a force on the segmented surface to thereby open the segmented surface.

In another embodiment, the invention is directed to a method for accessing the left atrium of a patient. The method comprises inserting the dilating tip of a device as described above into the right atrium of the patient. The atrial septum is punctured with the tube of the dilating tip to create a transseptal hole. The tubular body is advanced distally relative to the dilating tip to open the segmented surface and introduce a distal portion of the tubular body into the left atrium through the trans-septal hole.

DESCRIPTION OF THE DRAWINGS

These and other features and advantages of the present invention will be better understood by reference to the following detailed description when considered in conjunction with the accompanying drawings wherein:

FIG. 2 is a side view of a dilating tip according to the invention;

FIG. 3 is a side view of the dilating tip of FIG. 2 turned 90°;

FIG. 5 is a perspective view of a dilating tip mounted on the distal end of a tubular body, where the dilating tip is almost entirely open.

DETAILED DESCRIPTION OF THE INVENTION

The invention is directed to a device that serves as a guiding sheath, a dilator and a dilator needle. The device comprises a generally-flexible elongated tubular body 10 having proximal and distal ends and a lumen 12 extending longitudinally therethrough. In the depicted embodiment, the lumen 12 is a central lumen. The tubular body 10 can be of any suitable construction. Preferably the tubular body 10 comprises polyethylene with barium sulfate. If desired, a lubricious coating can be provided inside or over the tubular body 10. A suitable coating comprises silicone, such as MDX4-4159, a mixture of aminofunctional polydimethylsiloxane copolymer in mixed aliphatic and isopropanol solvents (commercially available from Dow Corning™, Midland, Mich.).

The tubular body 10 has an outer diameter ranging from about 2 mm to about 4 mm, preferably from about 2.5 mm to about 3.5 mm, still more preferably about 3 mm. Preferably the tubular body 10 has a length ranging from about 60 cm to about 100 cm.

Figure 1:
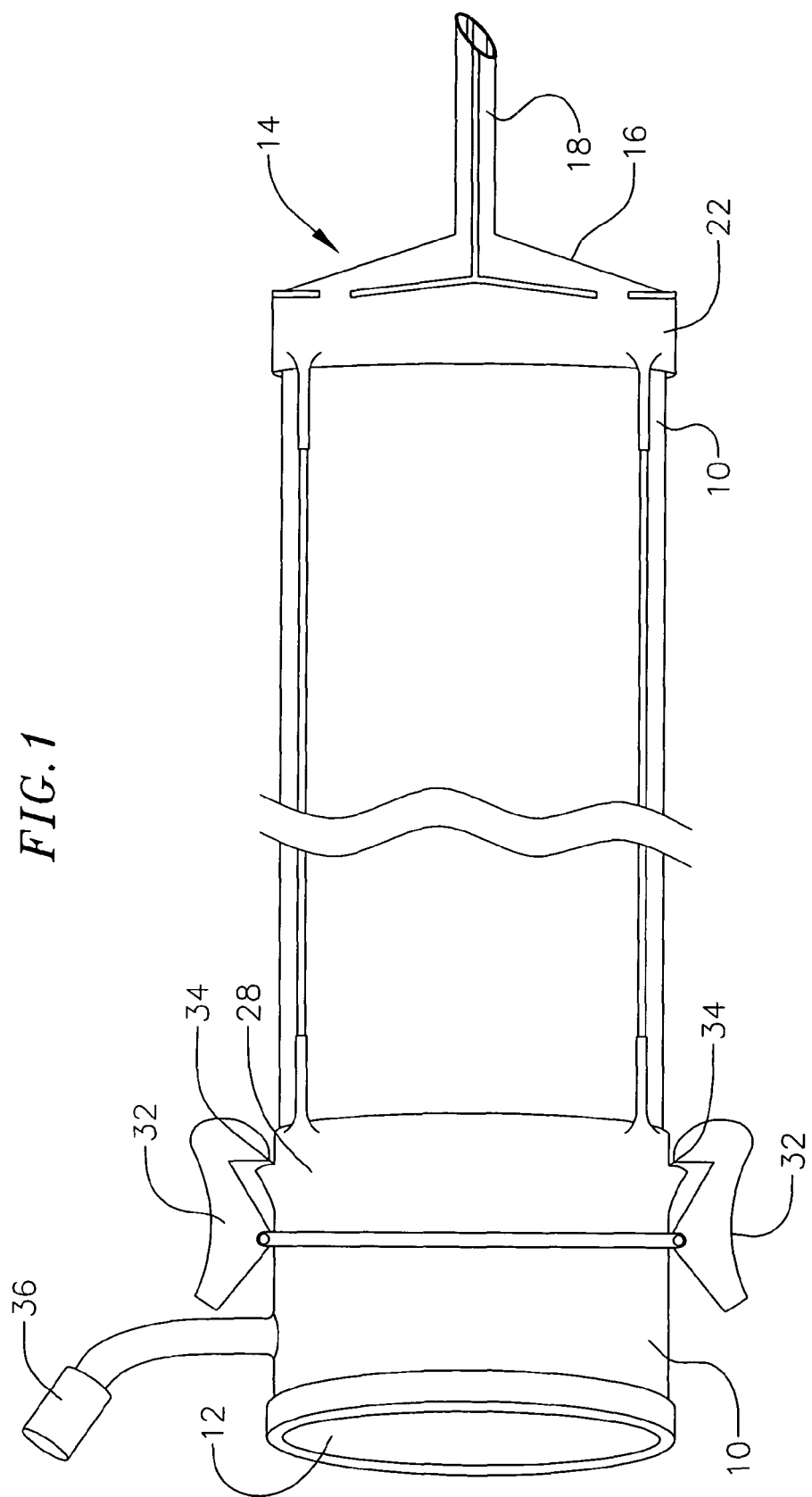
FIG. 1 is a perspective view of a device according to the invention.
Figure 4:
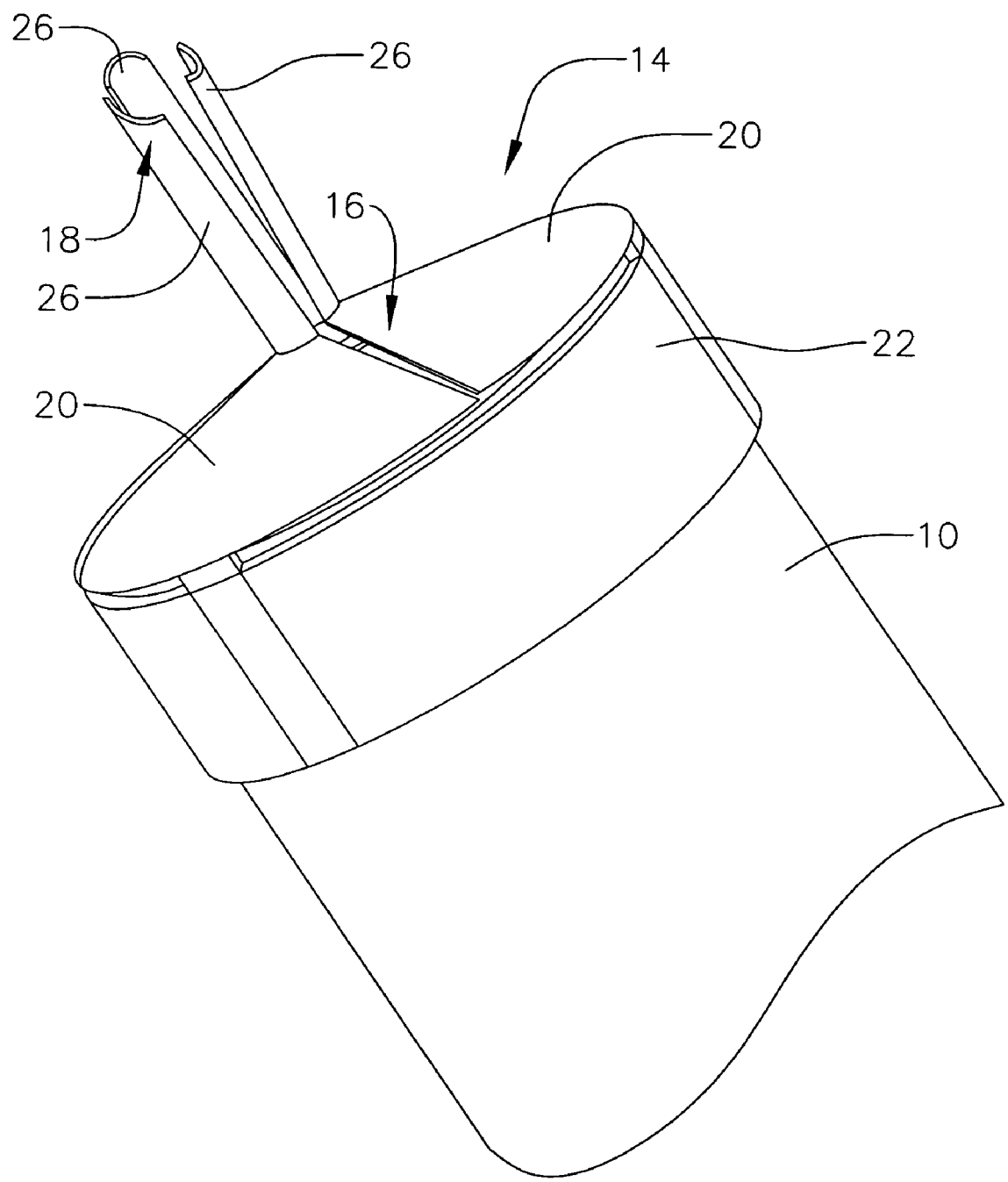
FIG. 4 is a perspective view of a dilating tip mounted on the distal end of a tubular body, where the dilating tip is slightly open.

On the distal end of the tubular body 10 is slidably mounted a dilating tip 14. As shown in FIGS. 2 to 5, the dilating tip 14 comprises a segmented surface 16 that is generally transverse to the axis of the tubular body 10, and a generally rigid tube 18 extending distally from the segmented surface. In the depicted embodiment, the dilating tip 14 is generally funnel-shaped with the segmented surface 16 being generally round and angled from its outer edge to its center, as best shown in FIGS. 2 and 3. The depicted segmented surface 16 comprises three pie-shaped segments 20, all of equal size. As will become apparent, the precise number, shape and size of the segments 20, as well as the overall shape of the dilating tip, can vary as desired. For example, the segmented surface 16 can be generally flat rather than angled, although the angled surface is particularly desirable for dilating the septum once the septum has been punctured, as described further below.

Preferably the dilating tip 14 is made from a material having shape memory. A particularly suitable material for this purpose is a memory alloy of a nickel-titanium composition known as nitinol. Type 55 nitinol, made of 55% by weight nickel and 45% titanium, and type 60 nitinol, made of 60% by weight nickel and 40% titanium, as well as various ternary and quaternary compositions of nitinol, can be used in the invention.

The dilating tip 14 further comprises a ring 22 slidably mounted over the outside of the tubular body 10 to which the segments 20 are attached. In the depicted embodiment, each of the segments 20 has an outer edge 21 that is hingedly attached to the ring 22 at a hinged junction 24. The segments 20 each also have two free edges 23 that are not attached to any of the other segments or to the ring 22. The ring 22 preferably has an inner diameter slightly greater than the outer diameter of the tubular body 10, and the inner diameter preferably ranges from about 2 mm to about 3 mm. As the ring 22 is moved proximally relative to the tubular body 10, the distal end of the tubular body contacts the inner surfaces of the segments 20 of the segmented surface 16, thereby pushing the segments distally 20. Because only the outer edges 21 of the segments 20 are hingedly attached to the ring 22, the tubular body 10 pushes the segments open, as best shown in FIG. 5.

As noted above, an elongated generally rigid tube 18 extends distally from the segmented surface 16. As best shown in FIG. 2, the generally rigid tube 18 has a sharp distal end 24. As used herein, the terms "generally rigid" and "sharp" when referring to the tube 18 and distal end 24, respectively, mean that the tube is sufficiently rigid and the distal end is sufficient sharp so that the tube can be used to puncture the septum, as described in more detail below. In the depicted embodiment, the tube 18 is depicted as generally cylindrical, but other shapes are contemplated within the invention, such as a tube having a generally square or hexagonal cross-sectional area. The tube 18 preferably has a length ranging from about 2 mm to about 6 mm, more preferably from about 3 mm to about 5 mm. The tube 18 preferably has an outer diameter ranging from about 0.6 mm to about 1 mm, more preferably from about 0.7 mm to about 0.8 mm.

In the depicted embodiment, the tube 18 is also segmented into three tube segments 26. Each tube segment 26 has a proximal end attached to a segment 20 and a free distal end. With this design, when the tubular body 10 is moved distally to open the segments 20, the tube segments 26 also separate and open with the segments 20. Other arrangements are contemplated within the scope of the invention. For example, the tube 18 could be a unitary (non-segmented) structure that is attached to only one of the segments 20.

In the depicted embodiment, the distal end of the tubular body 10 is generally straight. However, in some instances it may be advantageous for a portion of the distal end of the tubular body 10 to have a pre-formed curve. For example, due to the angle of the right atrium opening with respect to the atrial septum, when a tubular body 10 having a straight distal end is inserted into the right atrium and advanced to a position adjacent to the atrial septum, the tube 18 is likely to be angled with respect to the atrial septum. In such an instance, it may be desirable for the distal end of the tubular body 10 to have a pre-formed curve to allow the tube 18 to be situated in a more perpendicular arrangement relative to the atrial septum, thus allowing for a cleaner puncture of the septum.

In order to facilitate relative movement of the tubular body 10 relative to the dilating tip 14, a slidable ring 28 or other slidable member is mounted on the proximal end of the tubular body. The slidable ring 28 is connected to the ring 22 of the dilating tip 14 with a plurality of wires 30. Thus, in use, the physician can pull the slidable ring 28 proximally relative to the tubular body 10, thereby pulling the dilating tip 14 proximally relative to the tubular body, and thus opening the segmented surface 16 of the dilating tip. Other mechanisms for facilitating relative movement of the tubular body 10 and dilating tip 14 are considered within the scope of the invention.

In the depicted embodiment, a latch mechanism is provided to hold the slidable ring 28 in place relative to the tubular body 10 when the dilating tip 14 is in an open position. The latch mechanism includes one or more latches 32 that are fixedly attached to the proximal end of the tubular body 10 proximal to the slidable ring 28. The latches 32 are received by notches 34 in the slidable ring 28, to thereby temporarily lock the slidable ring in place. The presence and arrangement of the latch mechanism is not critical to the invention.

Additionally, a pressure valve 36 is mounted on the proximal end of the on the tubular body 10 such that the pressure in the tubular body may be monitored, as discussed further below.

In use, a guidewire (not shown), such as a 0.032 inch diameter guidewire, is positioned within the right atrium of a patient's heart. The device of the invention is then passed over the guidewire, with the guidewire extending through the lumen 12 of the tubular body 10 and through the elongated tube 18. The guidewire preferably includes an atraumatic distal tip.

The distal end of the device is passed over the guidewire and introduced into the right atrium. If desired, the dilating tip 14 and/or the distal end of the tubular body 10 can comprise tungsten or other radiopaque material, which appears dark under fluoroscopy, allowing the distal end of the device to be easily viewed under fluoroscopy. Once the dilating tip 14 is in the right atrium, a puncture site may be located. The limbus of the fossa ovalis provides a good reference point for locating an optimal puncture site. Often, the ridge of the limbus of the fossa ovalis can be felt by the operator using the distal end of the dilating tip 14. Just below the limbus is the central atrial septum, which tends to be the thinnest area of the septum, and is therefore the preferred area to penetrate. When the central atrial septum is located with the dilating tip 14, the tube 18 may be placed directly adjacent to and abutting the central atrial septum and pushed distally against the septum to thereby puncture of the septum.

As noted above, the proximal end of the tubular body 10 may be attached to a pressure valve 26 such that the pressure in the tubular body may be monitored. The pressure in the right atrium is different then the pressure in the left atrium. Therefore, by monitoring the pressure in the tubular body 10, the operator can determine when the needle has entered the left atrium, as is generally known in the art.

Once the tube 18 of the dilating tip 14 is in the left atrium, the slidable ring 28 on the proximal end of the tubular body 10 is moved distally relative to the tubular body. As a result, the distal end of the tubular body 10 is moved distally relative to the dilating tip 14 to thereby push open the segmented surface 16. This action dilates the trans-septal hole created with the tube 18 to thereby permit the distal end of the tubular body to be introduced into the left atrium. Alternatively, the segmented surface 16 can be moved distally into the left atrium to dilate the trans-septal hole, particularly when the segmented surface is angled as shown in FIGS. 2 and 3, before the tubular body 10 is moved distally to open the segmented surface.

Once the segmented surface 16 is opened within the left atrium, the latches 32 can then be used to maintain the slidable ring 28 in place so that the dilating tip 14 is kept in an open configuration. If the slidable ring 28 is not locked in place, the tubular body 10 may tend to slip proximally out of the left atrium. With the distal end of the tubular body 10 within the left atrium, the tubular body may then be used to guide a therapeutic catheter, such as an ablation catheter, into the left atrium. Thus, the tubular body 10 serves as a guiding sheath for this purpose.

The inventive device offers numerous advantages over devices previously used for trans-septal access. Notably, the inventive device avoids the need for a needle and dilator, as all of the functions are performed by the single device of the invention, thereby simplifying the process. In contrast, traditional methods require at least three different devices working together, thereby requiring numerous exchanges and management of fluids aspiration and pressure monitoring through more than one lure. The inventive device also avoids the need to change the pressure monitoring from a needle to a sheath.

Further, the limited length of the tube 18 avoids damage that can typically be caused when a needle is used and advanced too far into the left atrium. Additionally, the dilating tip 14, when in an open position, acts as a backstop to prevent the tubular body 10 from falling out of the left atrium. Therefore, it is not necessary to advance the tubular body 10 as far into the left atrium as is required with traditional guiding sheaths. As a result, the tubular body 10, which serves as a guide mechanism for a treatment catheter, does not significantly interfere with the operator's ability to manipulate the treatment catheter within the left atrium. In particular, the treatment catheter can be used to access more of the left atrium than with a traditional guiding sheath.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

The invention claimed is:

1. A device comprising:
an elongated, generally flexible tubular body; and
a dilating tip slidably mounted on a distal end of the tubular body and comprising:
a segmented surface comprising a plurality of segments having proximal and distal ends, wherein the plurality of segments is configured to move between a closed configuration in which the segments combine to form the segmented surface and an open configuration in which the segments separate from one another;
a plurality of generally rigid tube segments, each tube segment extending distally from a segment of the segmented surface, and wherein, when the plurality of generally rigid tube segments is in the closed configuration, the plurality of generally rigid tube segments combine to form a generally rigid tube having a sharp distal end configured to puncture tissue, and when the segments of the segmented surface are in the open configuration, the generally rigid tube segments have free distal ends that are separate from each other; and
a ring slidably mounted on the tubular body, wherein the proximal ends of the segments of the segmented surface are hingedly attached to the ring;
wherein proximal movement of the ring relative to the tubular body exerts a force on the segmented surface to thereby open the segmented surface.

2. A device according to claim 1, where the segmented surface comprises two or more segments.

3. A device according to claim 1, where the segmented surface comprises three or more segments.

4. A device according to claim 1, wherein the dilating tip is generally funnel-shaped.

5. A device according to claim 1, wherein the generally rigid tube of the dilating tip has a length ranging from about 2 mm to about 6 mm.

6. A device according to claim 1, wherein the generally rigid tube of the dilating tip has a length ranging from about 3 mm to about 5 mm.

7. A device according to claim 1, wherein the generally rigid tube of the dilating tip has an outer diameter ranging from about 0.6 mm to about 1 mm.

8. A device according to claim 1, wherein the generally rigid tube of the dilating tip has an outer diameter ranging from about 0.7 mm to about 0.8 mm.

9. A device according to claim 1, wherein the dilating tip comprises nitinol.

10. A device according to claim 1, further comprising a wire extending proximally from the dilating tip to near the proximal end of the tubular body to effect proximal movement of the dilating tip relative to the tubular body.

11. A device according to claim 10, further comprising a slidable member on the proximal end of the tubular body, the slidable member being connected to the wire so that proximal movement of the slidable member pulls the wire and causes proximal movement of the dilating tip relative to the tubular body.

12. A device according to claim 11, further comprising a latch for maintaining the position of the slidable member relative to the tubular body when the dilating tip is in the open configuration.

13. A device according to claim 1, further comprising a pressure valve at or near the proximal end of the tubular body.

14. A device comprising:
   an elongated, generally flexible tubular body;
   a dilating tip slidably mounted on a distal end of the tubular body and comprising:
      a ring mounted in surrounding relation to the distal end of the tubular body;
      a segmented surface comprising three or more segments, each segment being hingedly attached to the ring, wherein the three or more segments are configured to move between a closed configuration in which the segments combine to form the segmented surface and an open configuration in which the segments separate from one another; and
      three or more generally rigid tube segments, each tube segment extending distally from one of the three or more segments of the segmented surface, wherein when the three or more generally rigid tube segments are in the closed configuration, the three or more generally rigid tube segments combine to form a generally rigid tube having a sharp distal end configured to puncture tissue, and when the segments of the segmented surface are in the open configuration, the generally rigid tube segments have free distal ends that are separate from each other;
   a slidable member connected to the ring of the dilating tip, wherein proximal movement of the slidable member relative to the tubular body exerts a force on the segmented surface and the generally rigid tube to thereby open the segmented surface and the generally rigid tube.

15. A device according to claim 14, wherein the slidable member is connected to the ring of the dilating tip by a wire having a distal end attached to the ring of the dilating tip and a proximal end attached to the slidable member;
   wherein proximal movement of the slidable member pulls the wire and causes proximal movement of the dilating tip relative to the tubular body.

16. A device according to claim 14, further comprising a latch for maintaining the position of the slidable member relative to the tubular body when the dilating tip is in the open configuration.

17. A device according to claim 14, further comprising a pressure valve at or near the proximal end of the tubular body.

* * * * *